United States Patent
Chen et al.

(10) Patent No.: US 10,016,765 B2
(45) Date of Patent: Jul. 10, 2018

(54) METHOD FOR ADVANCING NON-MAGNETICALLY RESPONSIVE FUNCTIONAL AGENT

(71) Applicant: National Chiao Tung University, Hsinchu (TW)

(72) Inventors: Ching-Yao Chen, Taichung (TW); Yan-Hom Li, Taoyuan (TW); Ren-Chiuan Shiu, Taoyuan (TW)

(73) Assignee: National Chiao Tung University, Hsinchu (TW)

( * ) Notice: Subject to any disclaimer, the term of this patent is extended or adjusted under 35 U.S.C. 154(b) by 6 days.

(21) Appl. No.: 15/414,039

(22) Filed: Jan. 24, 2017

(65) Prior Publication Data

US 2018/0099292 A1    Apr. 12, 2018

(30) Foreign Application Priority Data

Oct. 12, 2016 (TW) .............................. 105132867 A

(51) Int. Cl.
| | |
|---|---|
| *B03C 1/24* | (2006.01) |
| *C02F 1/48* | (2006.01) |
| *B01L 3/00* | (2006.01) |
| *A61M 37/00* | (2006.01) |

(52) U.S. Cl.
CPC ............... *B03C 1/24* (2013.01); *A61M 37/00* (2013.01); *B01L 3/50273* (2013.01); *B01L 2400/043* (2013.01); *B03C 2201/18* (2013.01); *B03C 2201/20* (2013.01); *B03C 2201/26* (2013.01); *C02F 1/48* (2013.01)

(58) Field of Classification Search
CPC .................................................. B03C 2201/26

USPC .................................................. 204/557, 660
See application file for complete search history.

(56) References Cited

U.S. PATENT DOCUMENTS

2008/0014442 A1 *   1/2008   Rida .................. G01N 33/5434
                                                    428/403

FOREIGN PATENT DOCUMENTS

| TW | I241273 B | 10/2005 |
|---|---|---|
| TW | I311610 B | 7/2009 |
| TW | I394984 B | 5/2013 |

OTHER PUBLICATIONS

Rajesh Duggirala and Amit Lal. "A Hybrid PZT-Silicon Microvalve." Journal of Microelectromechanical Systems, vol. 14, No. 3, Jun. 2005. pp. 488-497.

(Continued)

*Primary Examiner* — Brian W Cohen
(74) *Attorney, Agent, or Firm* — Pepper Hamilton LLP

(57) ABSTRACT

A method for advancing a non-magnetically responsive functional agent includes steps (a) and (b). In step (a), a magnetically responsive agent construct at a target site is subjected to a homogeneous static magnetic field such that magnetically responsive micro particles are aligned to obtain a magnetic chain while the non-magnetically responsive functional agent is separated and discrete from the magnetic chain. In step (b), the magnetic chain is subjected to a rotational magnetic field to cause repeating breaking up and reformation of the magnetic chain such that the non-magnetically responsive functional agent is displaced to a predetermined position.

8 Claims, 8 Drawing Sheets

(56) References Cited

OTHER PUBLICATIONS

Alex Terray, et al. "Microfluidic Control Using Colloidal Devices." Science, vol. 296. Jun. 2002. pp. 1841-1844.
Li Zhang, et al. "Controlled Propulsion and Cargo Transport of Rotating Nickel Nanowires near a Patterned Solid Surface." American Chemical Society, Nano, vol. 4, No. 10, 2010. pp. 6228-6234, along with an 8-page Supporting Information.

* cited by examiner

METHOD FOR ADVANCING NON-MAGNETICALLY RESPONSIVE FUNCTIONAL AGENT

CROSS-REFERENCE TO RELATED APPLICATION

This application claims priority from Taiwanese patent application no. 105132867, filed on Oct. 12, 2016.

FIELD

The disclosure relates to a method for advancing a non-magnetically responsive functional agent, more particularly to a method for advancing a non-magnetically responsive functional agent using magnetically responsive micro particles.

BACKGROUND

Micro-Total analysis systems or lab-on-a-chip systems, in which a microfluidic device attracts more attention, are expected to be widely used in the medical examination and diagnosis field. In the microfluidic device, it is necessary to pump and direct fluids at very small length scale, and the fluids may be pumped and directed using a mechanical approach or a non-mechanical approach.

Alex Terray et al. in an article entitled "microfluidic control using colloidal devices," Science 7 Jun. 2002: Vol. 296, Issue 5574, pp. 1841-1844, describe that micrometer-scale fluid pumps and particulate valves are created by manipulating colloidal microspheres within customized channels.

Li Zhang et al. in an article entitled "Controlled Propulsion and Cargo Transport of Rotating Nickel Nanowires near a Patterned Solid Surface," ACS NANO, 2010, vol. 4, no. 10, describe that rotating Ni nanowires are capable of propulsion and transport of colloidal cargo and the motion of the Ni nanowires can be precisely controlled using a uniform rotating magnetic field.

Furthermore, movement of magnetic beads under a magnetic field is discussed in the following articles: (1) He-Ching Lin et al., "Structural instability of an oscillating superparamagnetic micro-bead chain," Microfluid Nanofluid (2014) 17:73-84; (2) Tamal Roy et al., "Magnetic microsphere-based mixers for microdroplets," PHYSICS OF FLUIDS 21, 027101 2009; and (3) Y. Gao et al., "Numerical and experimental study of a rotating magnetic particle chain in a viscous fluid," PHYSICAL REVIEW E 86, 041503 (2012).

U.S. Pat. No. 8,651,113 discloses a method for delivering a therapeutic to target cells within a body using a controllable magnetic field generator. The therapeutic is contained in magnetically responsive therapeutic constructs.

SUMMARY

Therefore, an object of the disclosure is to provide a novel method for advancing a non-magnetically responsive functional agent using a non-contact approach. Such method may be used for delivering the non-magnetically responsive functional agent to target cells in a body. Alternatively, such method may be used for directing a non-magnetically responsive functional agent in a microfluidic device. With the provision of the novel method, the movement of the non-magnetically responsive functional agent in a predetermined direction can be easily achieved at relatively low cost.

According to the disclosure, a method for advancing a non-magnetically responsive functional agent after a magnetically responsive agent construct is led to a target site in a liquid medium includes the steps of:

(a) subjecting the magnetically responsive agent construct at the target site to a homogeneous static magnetic field such that magnetically responsive micro particles of the magnetically responsive agent construct in the liquid medium are aligned to obtain a magnetic chain while the non-magnetically responsive functional agent is separated and discrete from the magnetic chain; and (b) subjecting the magnetic chain to a rotational magnetic field to cause repeating breaking up and reformation of the magnetic chain such that in response to the repeating breaking up and reformation of the magnetic chain, the non-magnetically responsive functional agent is displaced to a predetermined position.

BRIEF DESCRIPTION OF THE DRAWINGS

Other features and advantages of the disclosure will become apparent in the following detailed description of the embodiments with reference to the accompanying drawings, in which.

DETAILED DESCRIPTION

Figure 1:
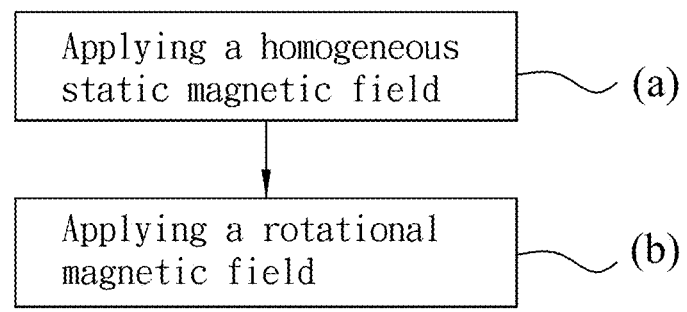
FIG. 1 is a block diagram illustrating a method for advancing a non-magnetically responsive functional agent according to the disclosure.
Figure 2:
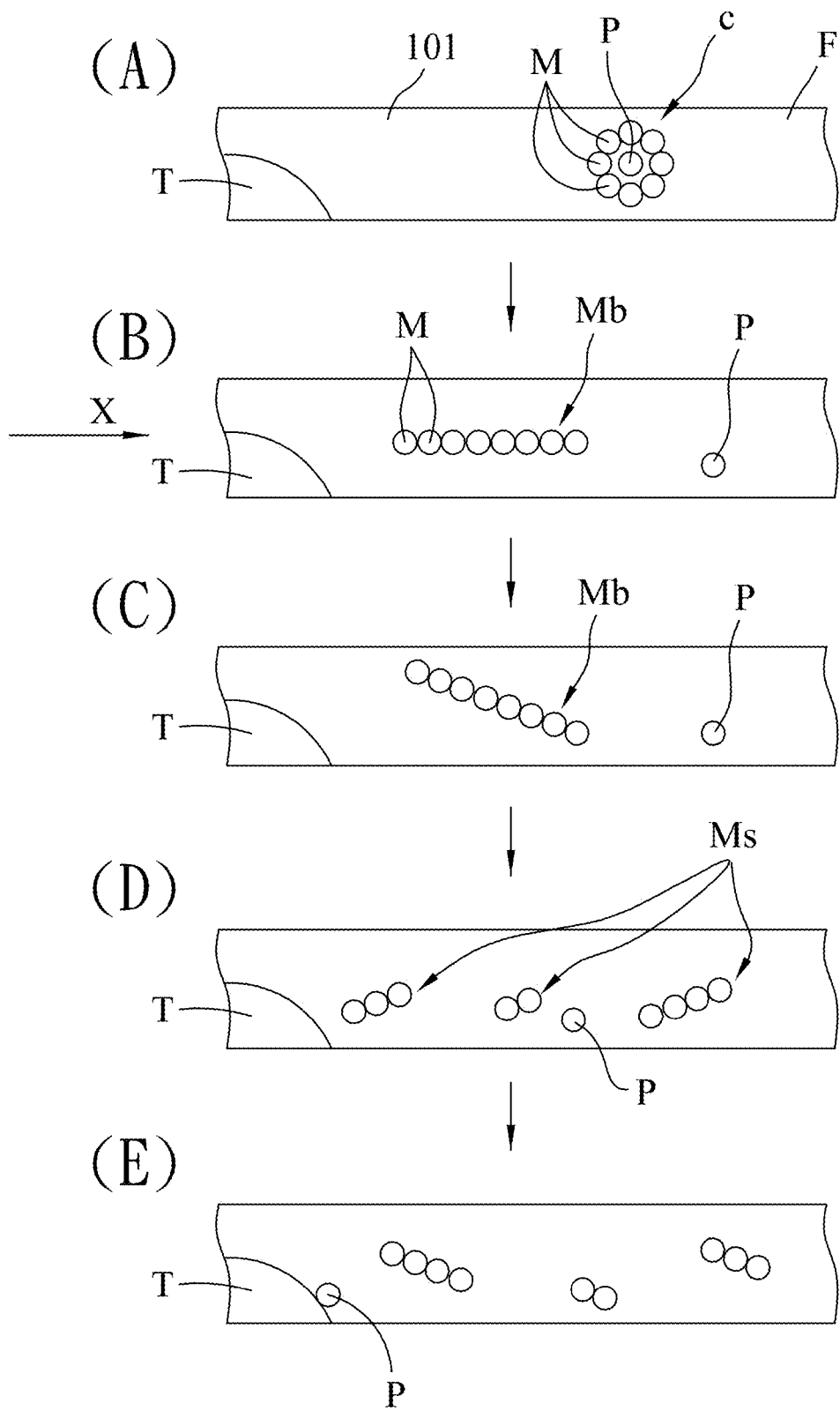
FIG. 2 is a flow diagram illustrating a method for advancing a non-magnetically responsive functional agent according to a first embodiment of the disclosure.

With reference to FIGS. 1 and 2, a method for advancing a non-magnetically responsive functional agent (P) according to a first embodiment of the disclosure is shown. The method is conducted after a magnetically responsive agent construct (C) is led to a target site in a liquid medium (F) which is filled, in a microfluidic channel 101. The microfluidic channel 101 may be in a microfluidic device or a capillary blood vessel. The non-magnetically responsive functional agent (P) may be a treating agent (such as drug), a specimen for examination and diagnosis, or a fluid sample which is insoluble in the liquid medium (F).

The method includes steps (a) and (b).

In step (a), the magnetically responsive agent construct (C) at the target site (see FIG. 2(a)) is subjected to a homogeneous static magnetic field such that magnetically responsive micro particles (M) of the magnetically responsive agent construct (C) in the liquid medium (F) are aligned to obtain a magnetic chain (M) while the non-magnetically responsive functional agent (P) is separated and discrete from the magnetic chain (Mb) (see FIG. 2(b)). As shown in FIG. 2(b), the magnetic chain (Mb) extends along a direction (X) which is parallel to the advancing direction of the non-magnetically responsive functional agent (P).

Each of the magnetically responsive micro particles (M) includes a superparamagnetic material such as $Fe_3O_4$, FeCo, and may be insulating beads containing or coated with superparamagnetic material or superparamagnetic nanoparticles. The insulating beads may be made from epoxy, polystyrene (PS), silicon oxide ($SiO_2$), etc. The number of the magnetically responsive micro particles (M) in the magnetic chain (Mb) is not less than 5. The magnetically responsive micro particles (M) have an average particle size ranging from 3 microns to 6 microns.

In the first embodiment, the microfluidic channel 101 is embodied as a capillary blood vessel in a body. The non-magnetically responsive functional agent (P) is a treating agent for treating target cells (T) within the body, and is carried by and moved with the magnetically responsive agent construct (C) before the magnetically responsive agent construct (C) is led to the target site.

Figure 3:
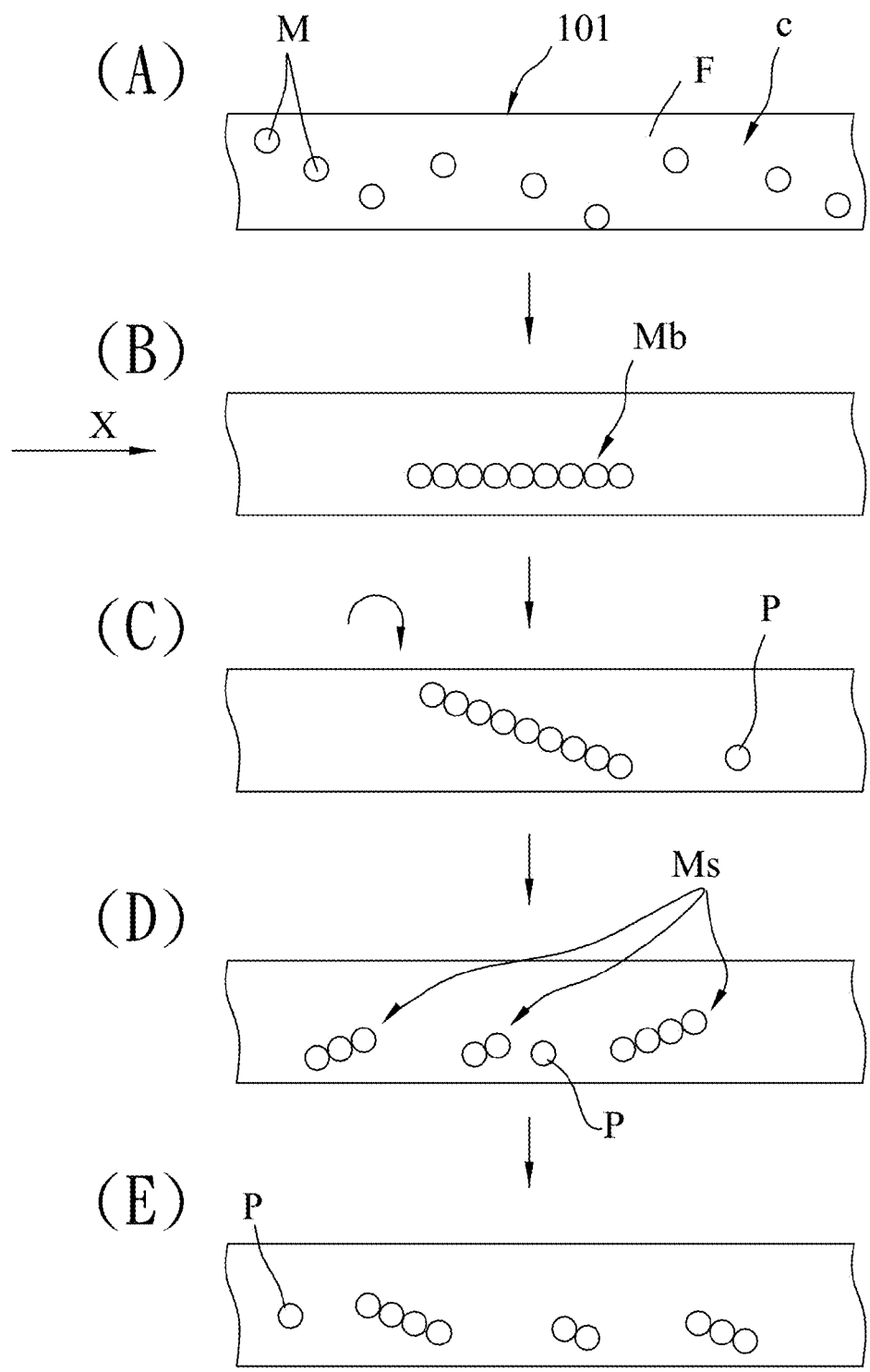
FIG. 3 is a flow diagram illustrating a method for advancing a non-magnetically responsive functional agent according to a second embodiment of the disclosure.

In a second embodiment of the disclosure, the microfluidic channel 101 may be embodied in a microfluidic device. As shown in FIG. 3(a), before step (a), the magnetically responsive agent construct (C) is led to the target side in the microfluidic channel 101 through an inlet 1011 of the microfluidic channel 101 (shown in FIG. 4), and the magnetically responsive micro particles (M) are dispersed in the liquid medium (F). Then, the homogeneous static magnetic field is applied to obtain the magnetic chain (Mb) as shown in FIG. 3(b). Thereafter, the non-magnetically responsive functional agent (P) is introduced into the microfluidic channel 101 through the inlet 1011 (see FIGS. 3(c) and 4).

In step (b), the magnetic chain (Mb) is subjected to a rotational magnetic field to cause repeating breaking up and reformation of the magnetic chain (Mb) such that in response to the repeating breaking up and reformation of the magnetic chain (Mb), the non-magnetically responsive functional agent (P) is displaced to a predetermined position (see FIGS. 2(c) to 2(e)).

Two sinusoidal fields with 90 degrees phase shift may be applied to generate the rotational magnetic field. Each of the two sinusoidal fields has a frequency not less than 1 Hz, and a magnetic field strength ranging from 14 Oe to 20 Oe. If the phase shift between two sinusoidal fields is not kept to 90 degrees, chain segments (Ms), which are formed after breaking up of the magnetic chains (Mb), may rotate at different speeds under the rotational magnetic field. In this case, the reformation of the magnetic chain (Mb) may be adversely affected.

In the first embodiment, in step (b), the non-magnetically responsive functional agent (i.e., the treating agent) (P) is displaced to the target cells (T) (see FIG. 2(e)).

In the second embodiment, in step (b), the non-magnetically responsive functional agent (i.e., the specimen or the fluid sample) (P) is moved toward the outlet 1012 (see FIGS. 3(c) to 3(e) and FIG. 4).

In addition to the rotational magnetic field, the rotation and breaking up of the magnetic chain (Mb) is also affected by the viscosity of the liquid medium (F), particle size and amounts of the magnetically responsive micro particles (M), etc. Rotating of the magnetic chain (Mb) under the rotational magnetic field involves competition between the induced viscous torque (Mv) and the magnetic torque (Mm), which defines the dimensionless Mason number (Mn):

$$Mn = \frac{\eta f}{\mu_0 \mu_s M^2}$$

in which $\eta$ is the viscosity of the liquid medium, f is the frequency of the rotational magnetic field, $\mu_0$ is the permeability of the rotational magnetic field in vacuum, $\mu_s$ is the permeability of the rotational magnetic field in the liquid medium, and M is the magnetization of the magnetically responsive micro particles.

During rotating, if the attractive forces among the magnetically responsive micro particles (M) of the magnetic chain (Mb) cannot overcome the inertia and the drag force in the liquid medium (F), the magnetic chain (Mb) would break up. To ensure the repeating breaking up and reformation of the magnetic chain (Mb), the Mason number (Mn) is controlled to range from 0.012 to 0.03.

The embodiments of the disclosure will now be explained in more detail below by way of the following examples.

Figure 4:
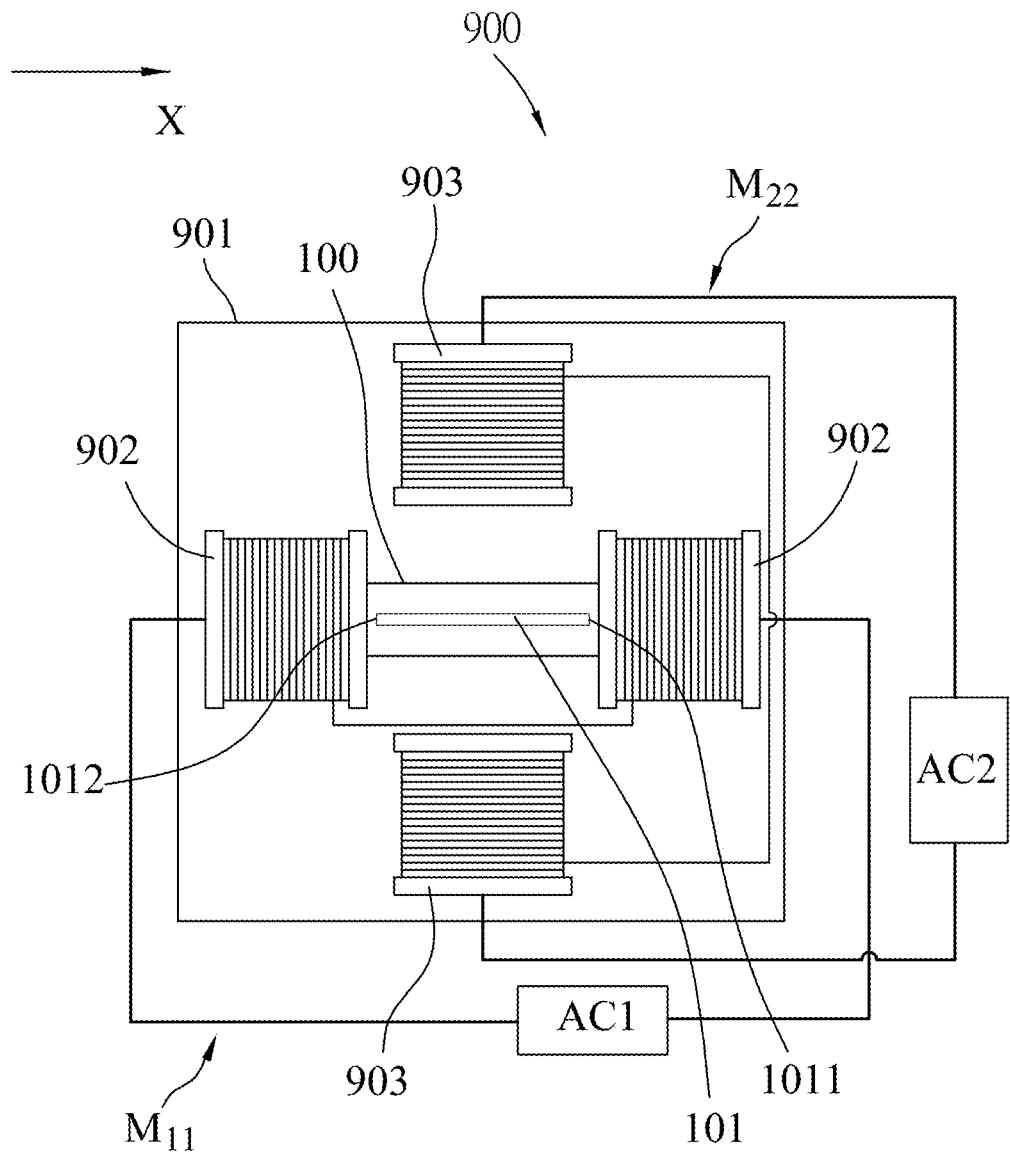
FIG. 4 is a schematic view illustrating a device for generating a rotational magnetic field.

A magnetic field generating device 900 shown in FIG. 4 was used for observation the repeating breaking up and reformation of the magnetic chain (Mb). The magnetic field generating device 900 includes a stage 901, a first module M11, and a second module M22. The first module M11 includes a first pair of electromagnetic coils 902 and a first power source (AC1). The second module M22 includes a second pair of electromagnetic coils 903 and a second power source (AC2). The stage 901 has a central region and a surrounding region which surrounds the central region. The first and second pairs of electromagnetic coils 902, 903 are disposed on the surrounding region and are displaced from one another in a circumferential direction. The first pair of electromagnetic coils 902 are spaced apart from each other in the direction (X) and are electrically connected to the first power source (AC1). The second pair of electromagnetic coils 903 are spaced apart from each other in a direction perpendicular to the direction (X), and electrically connected to the second power source (AC2). The first power source (AC1) can be switched to supply a DC current or an AC current. The second power source (AC2) can supply an AC current.

Example 1

A transparent chip 100 was disposed on the central area of the stags 901. The transparent chip 100 has an elongated microfluidic channel 101 which has an inlet 1011 and an outlet 1012, and which extends in the direction (X). A liquid medium, in which magnetically responsive micro particles (M) were dispersed, was introduced into the elongated microfluidic channel 101 via the inlet 1011. Then, a DC current from the first power source (AC1) was supplied to the first pair of electromagnetic coils 902 to generate a homogeneous static magnetic field such that the magnetically responsive micro particles (M) were aligned to obtain a magnetic chain (Mb). In Example 1, the liquid medium was distilled water, and the magnetically responsive micro particles (M) were polystyrene (PS) micro beads coated with $Fe_3O_4$. The magnetic chain (Mb) had eight magnetically responsive micro particles (M), and the particle size of the magnetically responsive micro particles (M) was about 4.5 microns. The magnetic field strength of the homogeneous static magnetic field was 39 Oe.

A non-magnetically responsive functional agent (P), which is a fluorescently-tagged polymer of 4.4 microns, was introduced into the elongated microfluidic channel 101 via the inlet 1011. Thereafter, the first power source (AC1) was turned off. Next, a first AC current from the first, power source (AC1) was supplied to the first pairs of electromagnetic coils 902 to generate a first sinusoidal field, and a second AC current from the second power source (AC2) was supplied to the second pairs of electromagnetic coils 903 to generate a second sinusoidal field. Each of the first and second sinusoidal fields had a frequency not less than 1 Hz and a magnetic field strength of 14.6 Oe. A rotational magnetic field was formed using the first and second sinusoidal fields. Under the rotational magnetic field, the magnetic chain (Mb) rotated in a clockwise direction, and broken into chain segments (Ms). At the same time, the non-magnetically responsive functional agent (P) is moved toward the outlet 1012.

Figure 5:
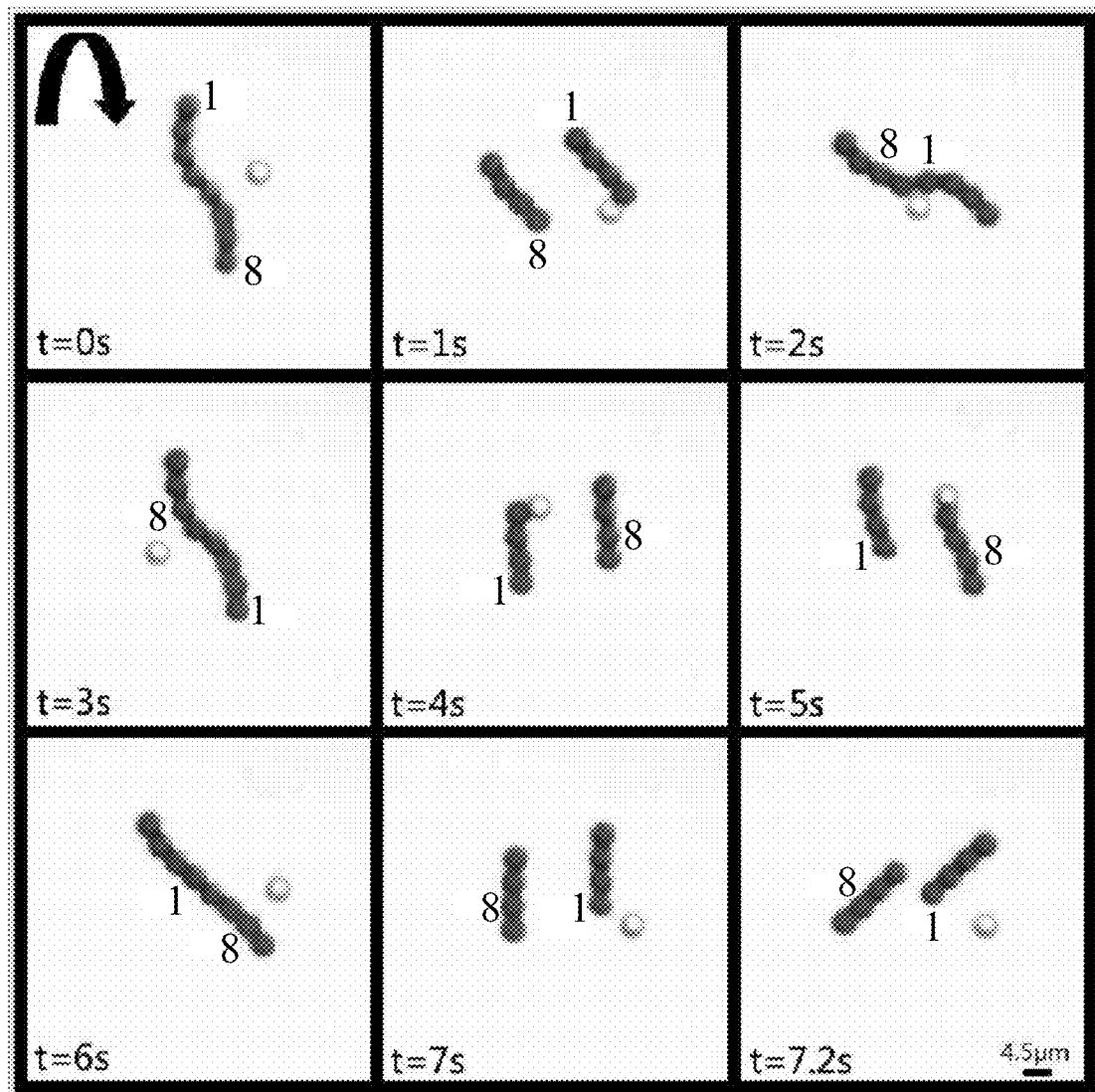
FIG. 5 shows sequential optical microscope images of a magnetic chain of Example 1 subjected to a rotational magnetic field at different times.
Figure 7:
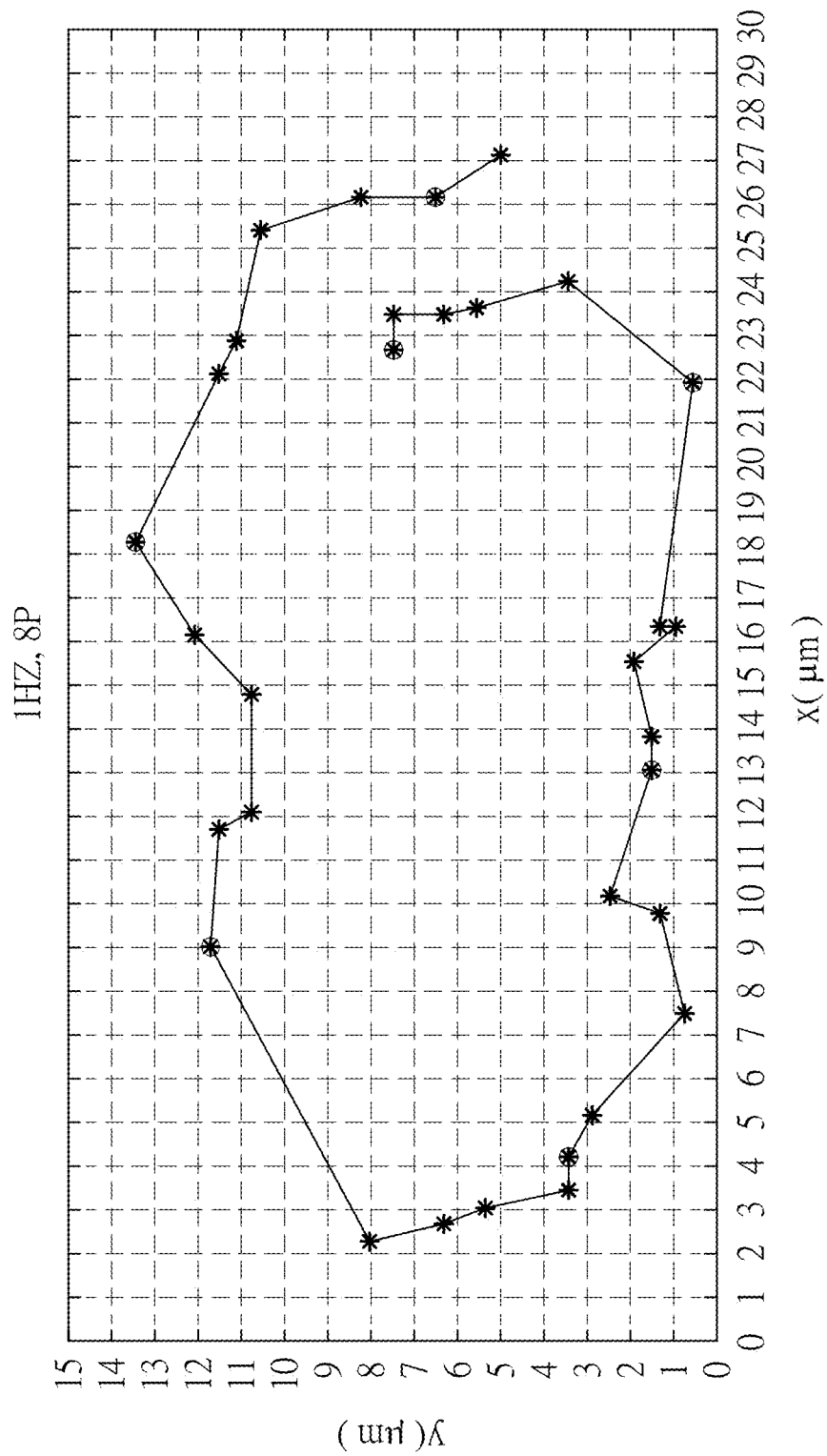
FIG. 7 shows a trajectory of a non-magnetically responsive functional agent of Example 1 during a time period when the magnetic chain of Example 1 was subjected to the rotational magnetic field.

Sequential optical microscope images of the magnetic chain (M1) are shown in FIG. 5, and the first and eighth magnetically responsive micro particles (M) are marked in FIG. 5. A trajectory of the non-magnetically responsive functional agent (P) is shown in FIG. 7.

Example 2

Figure 6:
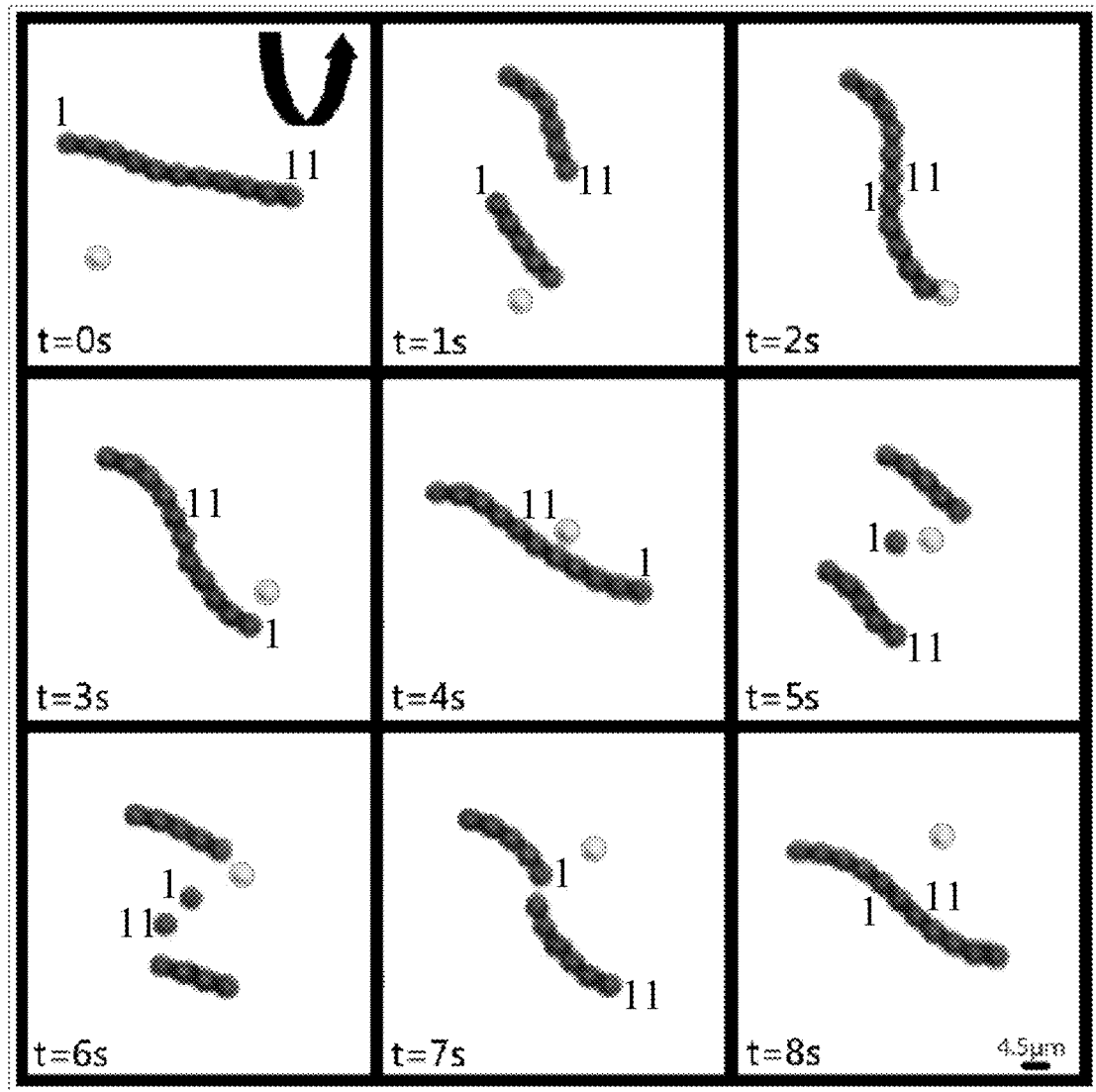
FIG. 6 shows sequential optical microscope images of a magnetic chain of Example 2 subjected to a rotational magnetic field at different times.

A magnetic chain (Mb) of Example 2 was prepared according to those described in Example 1. The magnetic chain (Mb) in Example 2 had eleven magnetically responsive micro particles (M). In Example 2, the magnetic field direction of each of first and second sinusoidal fields was set opposite to the magnetic field direction of each of first and second sinusoidal fields of Example 1. Therefore, the magnetic chain (Mb) in Example 2 rotated in a counterclockwise direction under the rotational magnetic field. Sequential optical microscope images of the magnetic chain (M1) are shown in FIG. 6, and the first and eleventh magnetically responsive micro particles (M) are marked in FIG. 6. A trajectory of the non-magnetically responsive functional agent (P) is shown in FIG. 8.

In FIGS. 5 and 6, repeating breaking up and reformation of the magnetic chain can be observed.

Figure 8:
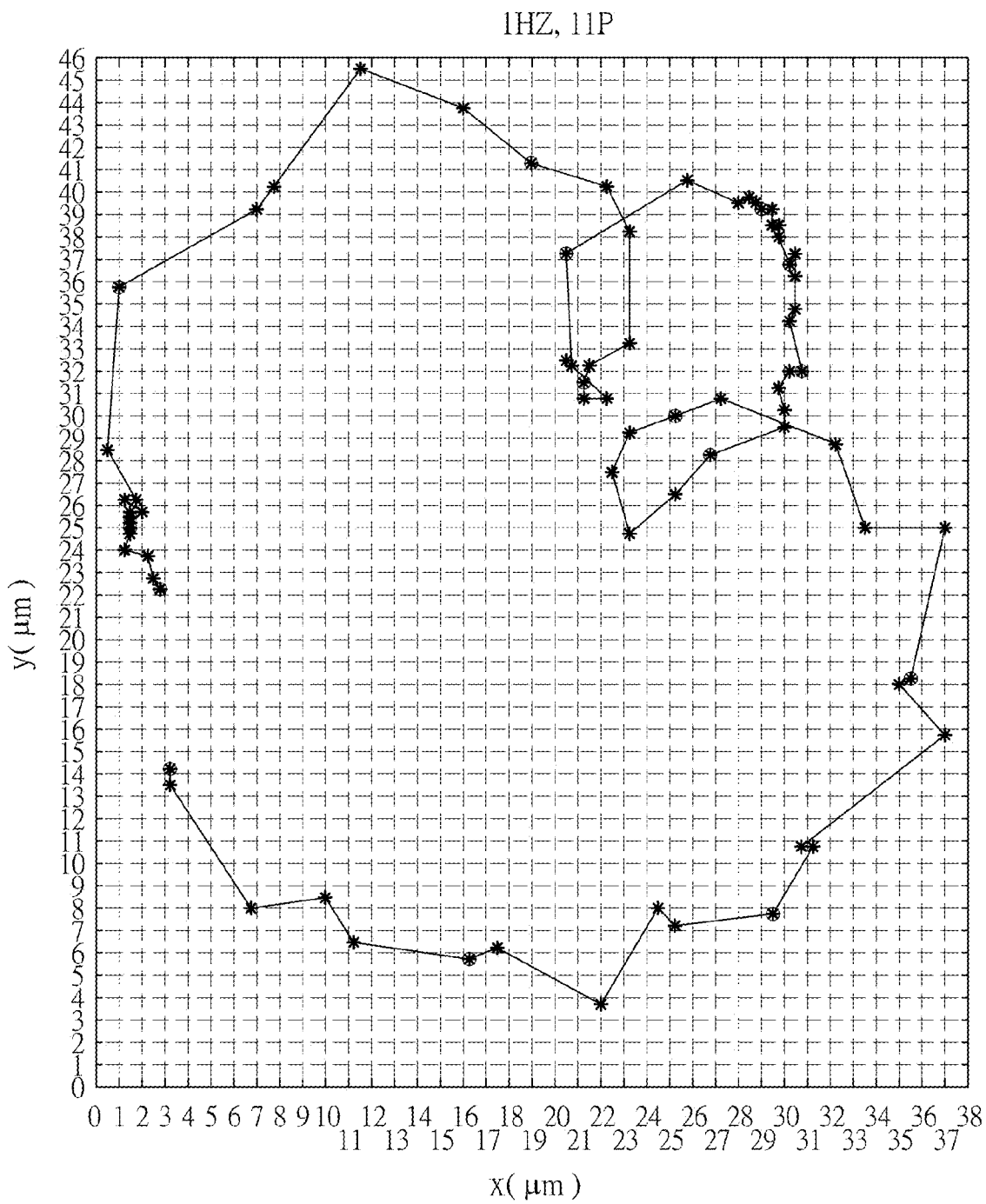
FIG. 8 shows a trajectory of a non-magnetically responsive functional agent of Example 2 during a time period when the magnetic chain of Example 2 was subjected to the rotational magnetic field.

In FIGS. 7 and 8, it can be observed that the more the number of the magnetically responsive micro particles (M) in the magnetic chain, the more the displacement of the non-magnetically responsive functional agent (P). In FIG. 7, the maximum displacement of the non-magnetically responsive functional agent (P) along the X-coordinate axis is 25 microns, and in FIG. 8, the maximum displacement of the non-magnetically responsive functional agent (P) along the X-coordinate axis is 37 microns.

Furthermore, a vortex, resulting from the rotation of the chain segments (Ms) of the magnetic chain (Mb), would cause the non-magnetically responsive functional agent (P) to move forth and back in a direction of the X-coordinate axis.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for advancing a non-magnetically responsive functional agent after a magnetically responsive agent construct is led to a target site in a liquid medium, the method comprising the steps of:
   (a) subjecting the magnetically responsive agent construct at the target site to a homogeneous static magnetic field such that magnetically responsive micro particles of the magnetically responsive agent construct in the liquid medium are aligned to obtain a magnetic chain while the non-magnetically responsive functional agent is separated and discrete from the magnetic chain; and
   (b) subjecting the magnetic chain to a rotational magnetic field to cause repeating breaking up and reformation of the magnetic chain such that in response to the repeating breaking up and reformation of the magnetic chain, the non-magnetically responsive functional agent is displaced to a predetermined position wherein the non-magnetically responsive functional agent is carried by and moved with the magnetically responsive agent construct before the magnetically responsive agent construct is let to the target site.

2. The method according to claim 1, wherein each of the magnetically responsive micro particles includes a superparamagnetic material.

3. The method according to claim 1, wherein the non-magnetically responsive functional agent is a treating agent for treating target cells within a body.

4. The method according to claim 1, wherein two sinusoidal fields with 90 degrees phase shift are applied to generate the rotational magnetic field.

5. The method according to claim 4, wherein each of the two sinusoidal fields has a frequency not less than 1 Hz, and a magnetic field strength ranging from 14 Oe to 20 Oe.

6. The method according to claim 1, wherein, in step (b), Mason number is controlled to range from 0.012 to 0.03.

7. The method according to claim 1, wherein the number of the magnetically responsive micro particles in the magnetic chain is not less than 5.

8. The method according to claim 1, wherein the magnetically responsive micro particles have an average particle size ranging from 3 microns to 6 microns.

* * * * *